US009468978B2

(12) United States Patent
Lo et al.

(10) Patent No.: US 9,468,978 B2
(45) Date of Patent: Oct. 18, 2016

(54) COLLAPSIBLE DRILL AND ASSOCIATED METHODS OF USE

(71) Applicant: Soteria Industries, Inc., Calgary (CA)

(72) Inventors: Ian K. Y. Lo, Calgary (CA); Paul Sciore, Calgary (CA); Ken Muldrew, Calgary (CA)

(73) Assignee: Soteria Industries, Inc., Calgary, AB (CA)

( * ) Notice: Subject to any disclaimer, the term of this patent is extended or adjusted under 35 U.S.C. 154(b) by 209 days.

(21) Appl. No.: 14/491,431

(22) Filed: Sep. 19, 2014

(65) Prior Publication Data

US 2015/0078849 A1    Mar. 19, 2015

Related U.S. Application Data

(60) Provisional application No. 61/880,174, filed on Sep. 19, 2013.

(51) Int. Cl.
*B23B 47/12* (2006.01)
*B23B 45/00* (2006.01)
(Continued)

(52) U.S. Cl.
CPC ............ *B23B 45/008* (2013.01); *B23B 31/302* (2013.01); *B23B 2260/044* (2013.01); *B23B 2260/0482* (2013.01); *B23B 2260/122* (2013.01); *B23B 2260/128* (2013.01); *B23B 2270/025* (2013.01); *B23B 2270/027* (2013.01); *B25D 9/12* (2013.01); *B25D 9/18* (2013.01); *B25D 11/005* (2013.01); *Y10T 408/03* (2015.01); *Y10T 408/04* (2015.01); *Y10T 408/15* (2015.01); *Y10T 408/165* (2015.01); *Y10T 408/18* (2015.01); *Y10T 408/20* (2015.01); *Y10T 408/65* (2015.01);
(Continued)

(58) Field of Classification Search
CPC ............ Y10T 408/665; Y10T 408/73; Y10T 408/75; Y10T 408/551; Y10T 408/18; Y10T 408/20; Y10T 408/15; A61B 17/16; A61B 17/1631; A61B 17/1695
USPC ................................ 173/2, 4, 11, 177, 13, 15
See application file for complete search history.

(56) References Cited

U.S. PATENT DOCUMENTS 1,711,427 A * 4/1929 Sauveur .................. B23B 31/38
                                                                     279/103
2,073,279 A   3/1937 Kinnear
(Continued)

OTHER PUBLICATIONS

International Search Report and Written Opinion of the International Searching Authority of PCT/ID2014/002687, mailed May 4, 2015.

*Primary Examiner* — Daniel Howell
*Assistant Examiner* — Yasir Diab
(74) *Attorney, Agent, or Firm* — Bryan D. Zerhusen; Locke Lord LLP

(57) ABSTRACT

The present disclosure provides exemplary collapsible drills and associated methods of use. Thus, in one aspect, the disclosure provides a collapsible drill including or comprising a chuck, a piston and a motor section. The chuck can be configured and dimensioned to receive a drill bit. The piston can include a pair of interlocking splines. The motor section drives rotation of the piston and the chuck. Depression of the piston can stop rotation of the chuck relative to the piston. In another aspect, the disclosure provides methods of drilling into a material that include providing a collapsible drill, driving rotation of the piston and the chuck with the motor section, and depressing the piston to stop rotation of the chuck relative to the piston.

20 Claims, 4 Drawing Sheets

(51) Int. Cl.
*B25D 9/12* (2006.01)
*B25D 9/18* (2006.01)
*B25D 11/00* (2006.01)
*B23B 31/30* (2006.01)

(52) U.S. Cl.
CPC ....... *Y10T408/665* (2015.01); *Y10T 408/6757* (2015.01); *Y10T 408/73* (2015.01); *Y10T 408/75* (2015.01)

(56) References Cited

U.S. PATENT DOCUMENTS

| | | | |
|---|---|---|---|
| 2,787,797 A * | 4/1957 | Kalafsky | B23G 1/46 192/46 |
| 2,978,047 A | 4/1961 | De Vaan | |
| 3,306,377 A | 2/1967 | Johnson | |
| 3,894,590 A | 7/1975 | Takano et al. | |
| 4,115,017 A * | 9/1978 | Wilhelmsson | B23B 49/003 408/14 |
| 4,273,481 A * | 6/1981 | Corley | B23B 49/003 408/12 |
| 4,286,676 A | 9/1981 | Nguyen et al. | |
| 4,530,625 A * | 7/1985 | Corley | B23B 49/003 408/10 |
| 4,824,255 A * | 4/1989 | Wohlrab | B29C 45/5008 366/100 |
| 5,485,853 A * | 1/1996 | Stubbs | A61B 10/0283 600/565 |
| 5,947,657 A * | 9/1999 | Lipohar | B23B 49/02 279/20 |
| 6,171,312 B1 * | 1/2001 | Beaty | A61B 17/1604 606/80 |
| 6,665,948 B1 * | 12/2003 | Kozin | A61B 17/1626 175/45 |
| 7,252,464 B2 * | 8/2007 | Goth | B23B 49/006 408/110 |
| 2008/0185793 A1 | 8/2008 | Haimer et al. | |
| 2010/0028097 A1 * | 2/2010 | Luepke | B23B 31/083 408/180 |
| 2012/0205131 A1 * | 8/2012 | Furusawa | B25D 16/006 173/2 |

* cited by examiner

COLLAPSIBLE DRILL AND ASSOCIATED METHODS OF USE

CROSS-REFERENCE TO RELATED APPLICATIONS

This application claims the benefit under 35 U.S.C. §119 (e) to U.S. Provisional Patent Application Ser. No. 61/880,174, titled: "Collapsible Drill and Associated Methods of Use", filed on Sep. 19, 2013, the disclosure of which is incorporated herein by reference in its entirety.

TECHNICAL FIELD

The present disclosure relates to collapsible drills and associated methods of use and, in particular, to collapsible drills which prevent spinning and/or advancing of a drill bit upon penetration of a drilled material.

BACKGROUND

Drilling holes within structures can be a common requirement in both medical and industrial fields. For example, in medical fields, drilling a hole through cartilage and/or bone may be desired. As a further example, in industrial fields, drilling a hole through wood, brick, steel and/or drywall may be desired. In general, a standard drill with a drill bit can be utilized to create the desired hole in the structure or material. Some traditional drills include a drill bit secured with a chuck which can be spun by a motorized system. Thus, any force or linear translation applied to the drill can be transferred directly to the drill bit.

Although the standard drill can be utilized successfully in sonic scenarios, in other scenarios, the depth of penetration of the drill bit in the structure or material can be critical. For example, in medical fields, structures such as blood vessels and/or nerves can exist behind the cartilage and/or bone being drilled and inadvertent injury to these structures can be catastrophic, e.g., vascular injury, neurologic damage, and the like. Similarly, in industrial fields, structures such as electrical wires can exist behind the material being drilled and inadvertent injury or penetration to these structures can be catastrophic or harmful to the user, e.g., electrocution injury, and the like. Thus, an inadvertent "plunging" of the drill bit, e.g., the drill bit traveling beyond the material being drilled, could lead to injury of the structures behind the material being drilled by the spinning drill bit itself and/or through direct penetration of the structure.

Traditionally, prevention of such injuries has been to allow the drill bit to travel only a fixed or predetermined distance, e.g., by utilizing a drill press or a similar device. However, in this method, the thickness of the material being drilled must be accurately known. In many scenarios, the thickness of the material being drilled may not be known to the user, e.g., drilling dry wall, or may be variable, e.g., curved bone. Thus, a common scenario involves drilling blindly whereby the distal surface, e.g., the inner surface, of the material being drilled is not visualized by the user. Therefore, the thickness of the material, e.g., the thickness of the bone, the current depth of penetration of the material by the drill bit and/or the structures behind the material being drilled, e.g., blood vessels, nerves, electrical wires, and the like, are not known.

Thus, a need exists for drills and associated methods which prevent spinning and/or advancing of a drill bit upon penetration of a structure. A further need exists for a drill and associated methods of use which retracts the drill bit of the drill away from the structures beyond the material being drilled upon penetration of the material. These and other needs are addressed by the collapsible drill and associated methods of use presently disclosed.

SUMMARY

The present disclosure provides exemplary collapsible drills and associated methods of use. Thus, in one aspect, the disclosure provides a collapsible drill including or comprising a chuck, a piston and a motor section. In an exemplary embodiment, the chuck is configured and dimensioned to receive a drill bit. In certain embodiments, the piston includes a pair of interlocking splines. In additional embodiments, the motor section drives rotation of the piston and the chuck. In some embodiments, depression of the piston stops rotation of the chuck relative to the piston.

In any of the embodiments described herein, the piston includes a piston rod linearly translatable within a cylinder. In some embodiments, the pair of interlocking splines includes a plurality of grooves on the cylinder configured to interlock or engage with a plurality of complementary teeth on the piston rod. In certain embodiments, the pair of interlocking splines includes a plurality of teeth on the cylinder configured to interlock or engage with a plurality of complementary grooves on the piston rod.

In additional embodiments, the piston rod includes a radial protrusion extending therefrom. In some embodiments, the cylinder includes an inner ledge configured and dimensioned to mate with the radial protrusion of the piston rod. In certain embodiments, the collapsible drill includes a seal, e.g., an O-ring, positioned between the radial protrusion and the inner ledge to form a sealed chamber within the cylinder.

In certain embodiments, the motor section includes a mechanism for filling the sealed chamber within the cylinder with compressed air. In certain embodiments, the motor section includes a mechanism for venting compressed air from the sealed chamber to atmosphere. In some embodiments, venting the compressed air from the sealed chamber to atmosphere depresses the piston rod into the cylinder. In additional embodiments, depressing the piston rod into the cylinder disengages the plurality of grooves and the plurality of complementary teeth of the pair of interlocking splines. In further embodiments, disengaging the plurality of grooves and the plurality of complementary teeth of the pair of interlocking splines stops rotation of the chuck relative to the piston, e.g., the cylinder of the piston.

In certain embodiments, depressing the piston rod into the cylinder automatically retracts the drill bit from the material. In some embodiments, the collapsible drill includes a second pair of interlocking splines positioned between the cylinder and the motor section.

In an additional aspect, the present disclosure provides exemplary methods of drilling into a material that include providing a collapsible drill as described herein. In certain embodiments, the exemplary methods include the step of driving rotation of the piston and the chuck with the motor section. In certain embodiments, the exemplary methods include depressing the piston to stop rotation of the chuck relative to the piston.

In additional embodiments, the exemplary methods include filling a sealed chamber within a cylinder of the piston with compressed air to position a radial protrusion extending from a piston rod against an inner ledge of the cylinder. In certain embodiments, the exemplary methods include maintaining a pressure within the sealed chamber to maintain the drill bit in an extended position.

In certain embodiments, the exemplary methods include interlocking or engaging a plurality of grooves on a cylinder of the piston with a plurality of complementary teeth on a piston rod of the piston of the pair of interlocking splines to drive rotation of the chuck relative to the piston. In certain embodiments, the exemplary methods include interlocking or engaging a plurality of teeth on a cylinder of the piston with a plurality of complementary grooves on a piston rod of the piston of the pair of interlocking splines to drive rotation of the chuck relative to the piston.

In additional embodiments, the exemplary methods include venting the sealed chamber to depress the piston rod into the cylinder. In some embodiments, depressing the piston rod into the cylinder further includes disengaging a plurality of grooves on the cylinder with a plurality of complementary teeth on the piston rod of the pair of interlocking splines. In some embodiments, depressing the piston rod into the cylinder further includes disengaging a plurality of teeth on the cylinder with a plurality of complementary grooves on the piston rod of the pair of interlocking splines.

In certain embodiments, disengaging the plurality of grooves on the cylinder with the plurality of complementary teeth on the piston rod of the pair of interlocking splines includes stopping rotation of the chuck relative to the piston. In certain embodiments, disengaging the plurality of teeth on the cylinder with the plurality of complementary grooves on the piston rod of the pair of interlocking splines includes stopping rotation of the chuck relative to the piston.

In certain embodiments, depressing the piston rod into the cylinder includes automatically retracting the drill bit from the material.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed collapsible drills and associated methods, reference is made to the accompanying figures, wherein.

DETAILED DESCRIPTION

Figure 1:
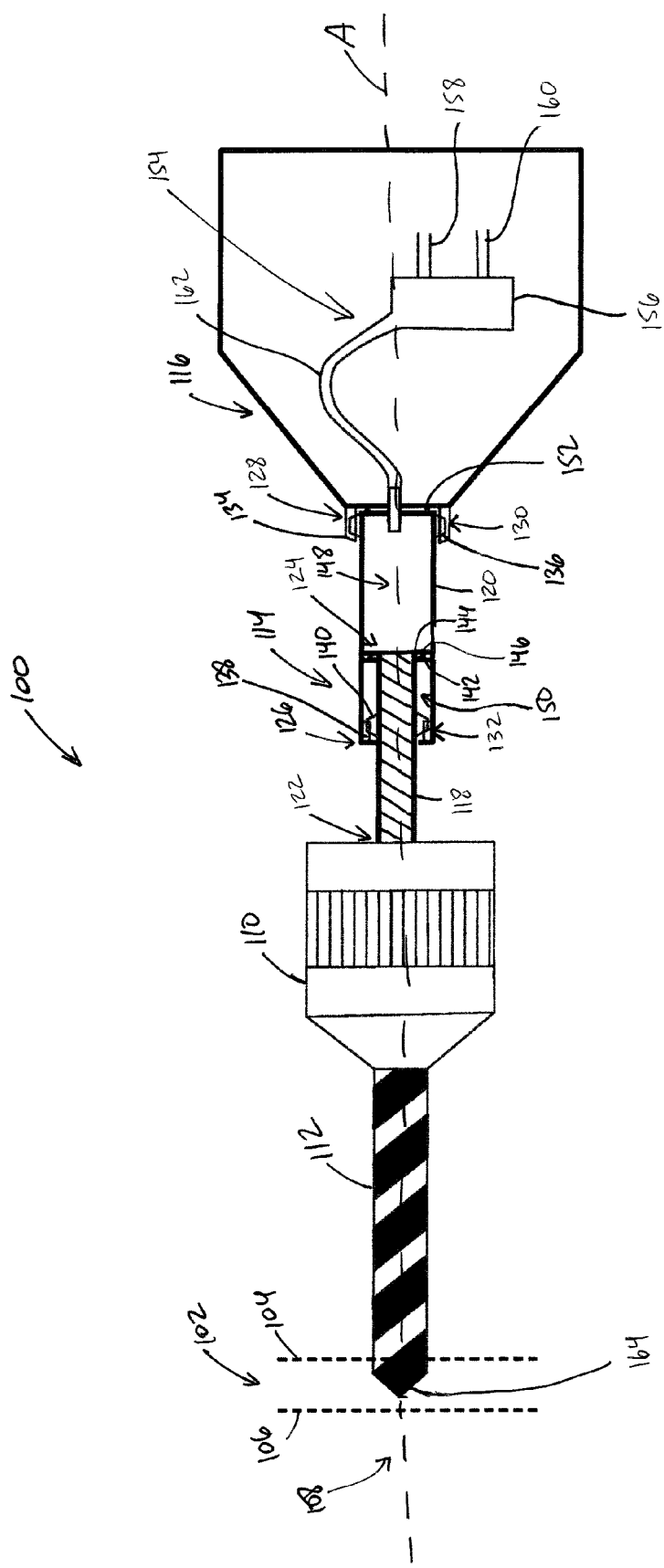
FIG. 1 shows a side, partial cross-sectional view of an exemplary collapsible drill in an extended and engaged position prior to complete penetration of a drilled material.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. Ranges from any lower limit to any upper limit are contemplated. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

The articles "a" and an as used herein and in the appended claims are used herein to refer to one or to more than one (i.e., to at least one) of the grammatical object of the article unless the context clearly indicates otherwise. By way of example, "an element" means one element or more than one element.

All numerical values within the detailed description and the claims herein are modified by "about" or "approximately" the indicated value, and take into account experimental error and variations that would be expected by a person having ordinary skill in the art.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., one or more of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as only one of or "exactly one of," or, When used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally he present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B'") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the 10 United States Patent Office Manual of Patent Examining Procedures, Section 2111.03.

Figure 2:
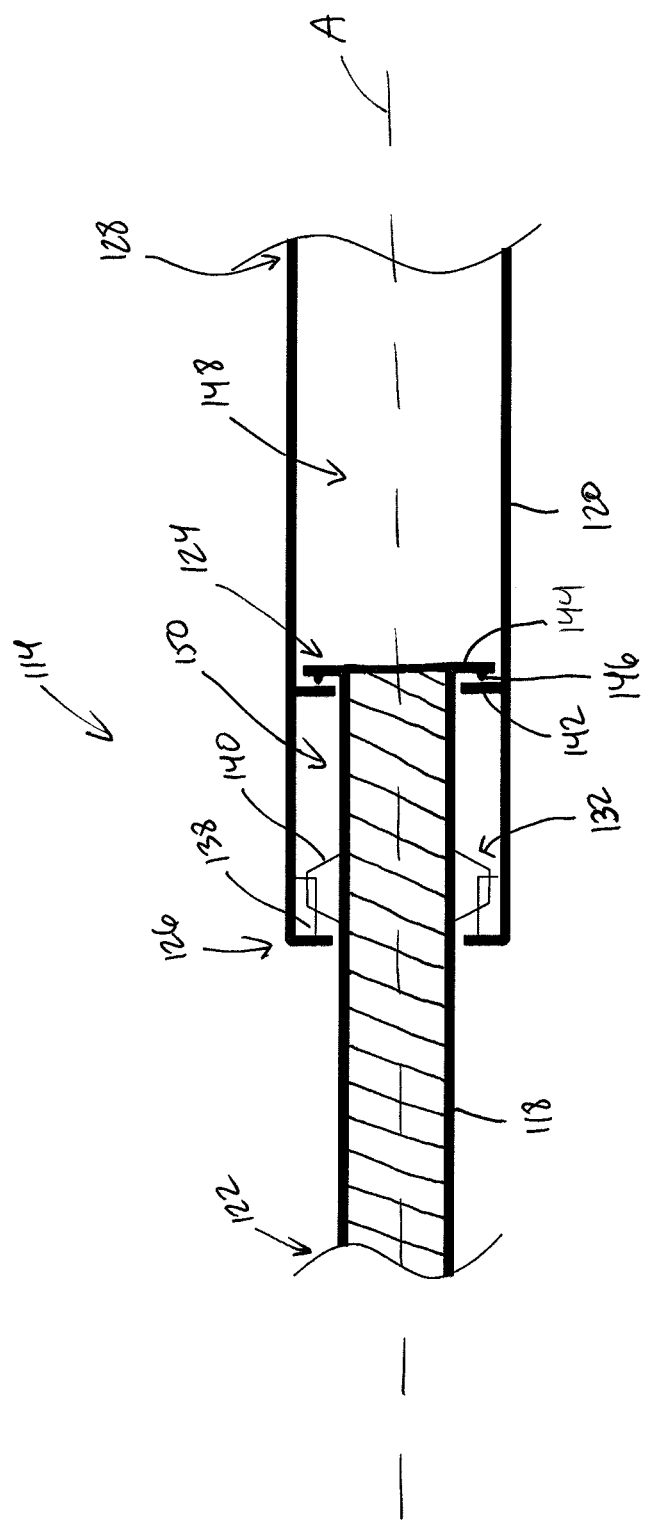
FIG. 2 shows a detailed side, cross-sectional view of an exemplary collapsible drill in an extended and engaged position prior to complete penetration of a drilled material.

With reference to FIGS. 1 and 2, side, partial and detailed cross-sectional views of an exemplary collapsible drill 100 (hereinafter "drill 100") are provided. In particular, drill 100 is schematically illustrated in an extended and engaged position prior to complete penetration of a drilled material 102, e.g., a wall, bone, cartilage, and the like. The drilled material 102 can define an outer surface 104, e.g., the surface through which the drill 100 begins to drill, and an inner surface 106, e.g., the surface at which, after penetration, it is desired to stop the drill 100 to prevent to prevent entrance of the drill 100 into an inner cavity 108. The inner cavity 108 can include one or more structures (not shown) therein, e.g., blood vessels, nerves, electrical wires, and the like, and prevention of plunging into the inner cavity 108 with the drill 100 is desired to prevent damage to the one or more structures.

The exemplary drill 100 includes a chuck 110 configured and dimensioned to receive and/or retain a drill bit 112 therein. It should be understood that the chuck 110 can receive a variety of drill bit 112 sizes as needed by a user. In some embodiments, the chuck 110 can be a standard chuck utilized in the industry. In some embodiments, the drill bit 112 can be a standard drill bit utilized in the industry. The drill 100 further includes a piston 114 and a motor section 116. The piston 114 includes a piston rod 118 and a cylinder 120 aligned along a central axis A. The piston rod 118 can define a distal end 122 and a proximal end 124. In some embodiments, the piston rod 118 can define a solid structure, e.g., a non-hollow structure. The cylinder 120 can define a distal end 126 and a proximal end 128.

The piston 114 can include a first pair of interlocking splines 130 and a second pair of interlocking splines 132. The first pair of interlocking splines 130 can be located at the proximal end 128 of the cylinder 120 and can provide an interlocking or engagement interface between the motor section 116 and the cylinder 120 of the piston 114. In some embodiments, the motor section 116 can include a plurality of grooves 134 radially spaced about the central axis A configured and dimensioned to interlock with a plurality of complementary teeth 136, e.g., ridges, radially spaced about the central axis A of the outer surface of the proximal end 128 of the cylinder 120. In some embodiments, the motor section 116 can include radially spaced teeth 136 and the proximal end 128 of the cylinder 120 can include radially spaced complementary grooves 134. The first pair of interlocking splines 130 allows torque to be transferred from the motor section 116 to the piston 114 to regulate rotation of the piston 114. For example, the motor section 116 can actuate or engage the grooves 134 to rotate about the central axis A which, in turn, actuate or engage the interlocked teeth 136 to rotate about the central axis A. Although not illustrated, those of ordinary skill in the art should understand that the motor section 116 includes a motor for creating the torque for rotating the grooves 134 of the first pair of interlocking splines 130.

The second pair of interlocking splines 132 can be located at the distal end 126 of the cylinder 120 and a midpoint between the distal end 122 and the proximal end 124 of the piston rod 118. The second pair of interlocking splines 132 can provide an interlocking or engagement interface between the piston rod 118 and the cylinder 118 of the piston 114. In some embodiments, an inner surface of the distal end 126 of the cylinder 120 can include a plurality of grooves 138 radially spaced about the central axis A configured and dimensioned to interlock with a plurality of complementary teeth 140, e.g., ridges, radially spaced about the central axis A of the outer surface of the piston rod 118. In some embodiments, the cylinder 120 can include radially spaced teeth 140 and the piston rod 118 can include radially spaced complementary grooves 138. The second pair of interlocking splines 132 allows torque coupling between the cylinder 118, the piston rod 118 and the chuck 110 by engaging the teeth 140 with the grooves 138. The torque from the motor section 116 can thereby be transferred to the chuck 110 to regulate rotation of the drill bit 112.

In some embodiments, the distal end 122 of the piston rod 118 can be secured to the chuck 110 and the proximal end 124 can be movably engaged with the cylinder 120 of the piston 114. In particular, the proximal end 124 of the piston rod 118 can he linearly translatable within the cylinder 120 along the central axis A. The cylinder 120 can include an inner radial ledge 142 located along the inner surface of the cylinder 120 at a midpoint between the distal end 126 and the proximal end 128 of the cylinder 120. The ledge 142, can extend from the inner surface of the cylinder 120 in the direction of the central axis A and can be configured to form a central aperture dimensioned to receive the piston rod 118 therethrough. The ledge 142 can act as a stop to limit translation of the piston rod 118 within the cylinder 120. For example, the piston rod 118 can translate within the cylinder 120 along the central axis A until the teeth 140 of the second pair of interlocking splines 132 engage the ledge 142.

The proximal end 124 of the piston rod 118 can include a radial protrusion 144 extended from the piston rod 118 and away from the central axis A. In particular, the proximal end 124 of the piston rod 118 can define a substantially flat surface extending across the entire diameter of the piston rod 118 and the radial protrusion 144 can further extend from the proximal end 124 surface away from the central axis A. The radial protrusion 144 can be configured and dimensioned to fit within the inner walls of the cylinder 120. In some embodiments, the radial protrusion 144 can include an O-ring 146 secured thereon. The piston rod 118 can be assembled with the cylinder 120 such that the radial protrusion 144 is positioned between the ledge 142 and the proximal end 128 of the cylinder 120. The piston rod 118 can thereby translate along the central axis A in the direction of the proximal end 128 of the cylinder 120 until the teeth 140 engage the ledge 142 and translate along the central axis A in the direction of the distal end 126 of the cylinder 120 until the radial protrusion 144 engages the ledge 142.

Engagement of the radial protrusion 144 with the ledge 142 can form a seal between a first chamber 148 and the second chamber 150 of the cylinder 120. The first chamber 148 can therefore be defined as the inner cavity of the cylinder 120 located between the proximal end 128 of the cylinder 120 and the radial protrusion 144 of the piston rod 118. The second chamber 150 can be defined as the inner cavity of the cylinder 120 located between the ledge 142 and the distal end 126 of the cylinder 120. In some embodiments, the drill 100 includes a sensor 152, e.g., a force transducer, positioned between the motor section 116 and the proximal end 128 of the cylinder 120. The sensor 152 can measure a reaction force from the drill bit 112 back to the motor section 116. For example, the sensor 152 can measure the pressure imparted by the drill bit 112 against the drilled material 102 such that a change in the reaction force can be detected by the sensor 152 when the drill bit 112 has passed through the inner surface 106 of the drilled material 102.

In some embodiments, the motor section 116 of the drill 100 can include a compressed air mechanism 154 therein. The compressed air mechanism 154 can include a compressor 156 with an inlet 158 and an outlet 160. The compressed air mechanism 154 can further include a hose 162, e.g., a flexible air hose, connecting the compressor 156 to the proximal end 128 of the cylinder 120. The compressor 156 can intake compressed air through the inlet 158 and pass the compressed air through the hose 162 into the first chamber 148 of the cylinder 120. The seal between the radial protrusion 144 and the ledge 142 can seal the first chamber 148 such that the compressed air can be maintained within the first chamber 148. The compressor 156 can further release the compressed air from the first chamber 148 through the hose 162 and out of the outlet 160.

Still with reference to FIGS. 1 and 2, when the drill 100 is positioned in an extended position for drilling, the piston rod 118 can be extended from the cylinder 120 such that the first and second pairs of interlocking splines 130, 132 are interlocked or engaged. In some embodiments, the piston rod 118 can be actuated into the extended position by filling or preloading the first chamber 148 with compressed air with the compressed air mechanism 154. For example, the compressed air can impart a force on the proximal end 124 surface and the radial protrusion 144 surface of the piston rod 118 to linearly translate the piston rod 118 in the direction of the ledge 142 and seal the radial protrusion 144 against the ledge 142. The compressed air area within the first chamber 148 can therefore impart and maintain a pressure against the radial protrusion 144 in the direction of the distal end 122 of the piston rod 118 to maintain the radial protrusion 144 and/or the O-ring 146 against the ledge 142, thereby maintaining the compressed air pressure within the first chamber 148.

Translation of the piston rod 118 into the extended position can interlock the grooves 138 and the teeth 140 of the second pair of interlocking splines 132. The first pair of interlocking splines 130 can therefore provide torque transfer from the motor section 116 to the cylinder 120 and the second pair of interlocking splines 132 can provide torque transfer from the cylinder 120 to the piston rod 118. The piston rod 118 can, in turn, provide torque to the chuck 110 and the drill bit 112.

In some embodiments, the first and/or second pair of interlocking splines 130, 132 can allow a small movement between the piston 114 and the motor section 116 of the drill 100. Based on the movement between the piston 114 and the motor section 116, the sensor 152 positioned between the piston 114 and the motor section 116 can measure the reaction force from the drill bit 112 back to the motor section 116. For example, when pressure is applied by the user performing the drilling in a linear and/or non-linear direction along the central axis A by pressing the tip 164 of the drill bit 112 and/or an area of the drill bit 112 adjacent to the tip 164 against the drilled material 102, the pressure can be measured by the sensor 152. As discussed above, the compressed air preloaded into the first chamber 148 with the compressed air mechanism 154 can maintain the piston 114 in the extended position.

During drilling, the pressure applied by the user against the drill bit 112 can vary. The compressed air mechanism 154 can therefore intake additional compressed air through the inlet 158 and into the first chamber 148 as needed to maintain or increase the compressed air pressure within the first chamber 148 of the piston 114 to resist the application of linear pressure and to maintain the piston 114 in the extended position. In some embodiments, the compressed air mechanism 154 can include a sensor (not shown) to detect the pressure within the first chamber 148. Maintaining or increasing the pressure within the first chamber 148 of the piston 114 can maintain the interlock or engagement between the grooves 138 and the teeth 140 of the second pair of interlocking splines 132. Torque can therefore be transferred from the motor section 116 to the piston 114, the chuck 110 and the drill bit 112. The drill bit 112 can thereby be rotated at the desired speed and can be advanced through the drilled material 102.

Figure 3:
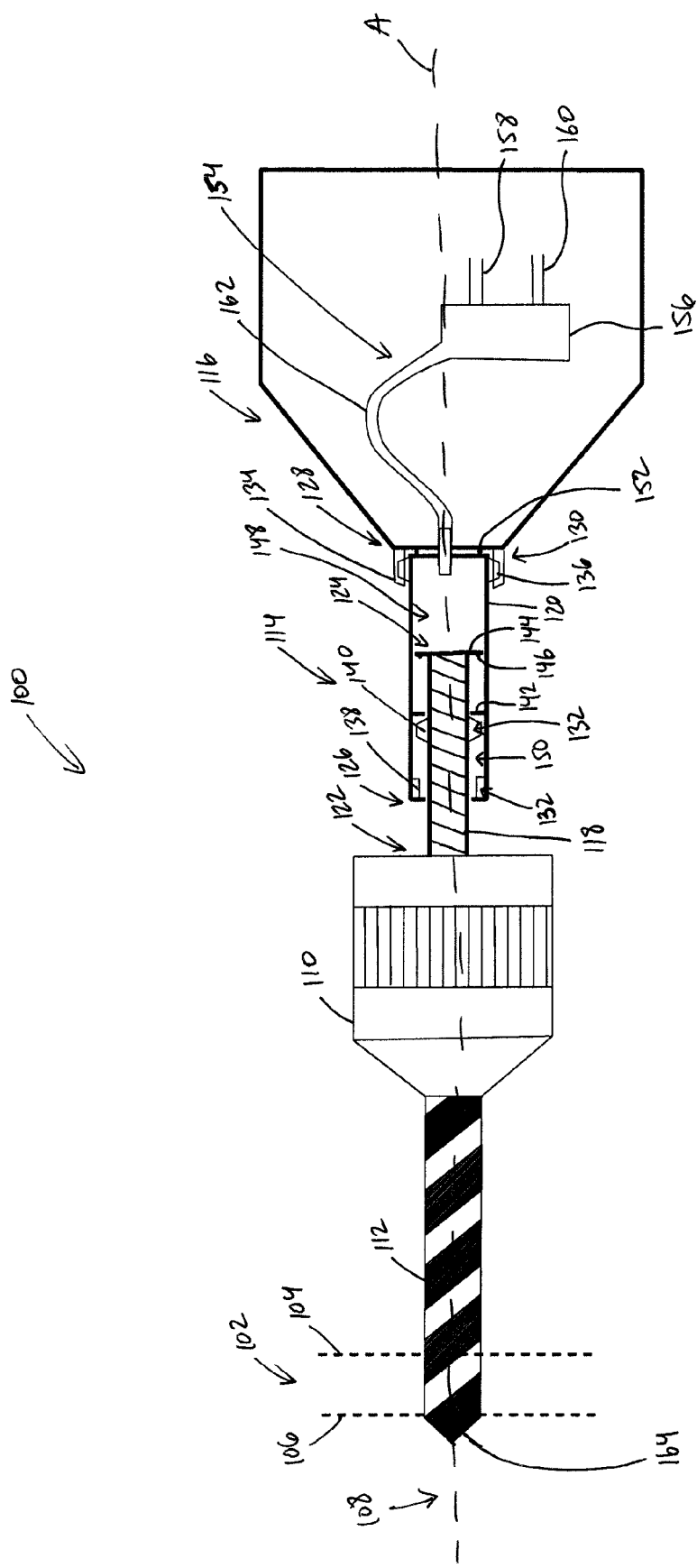
FIG. 3 shows a side, partial cross-sectional view of an exemplary collapsible drill in a collapsed and disengaged position after complete penetration of a drilled material.
Figure 4:
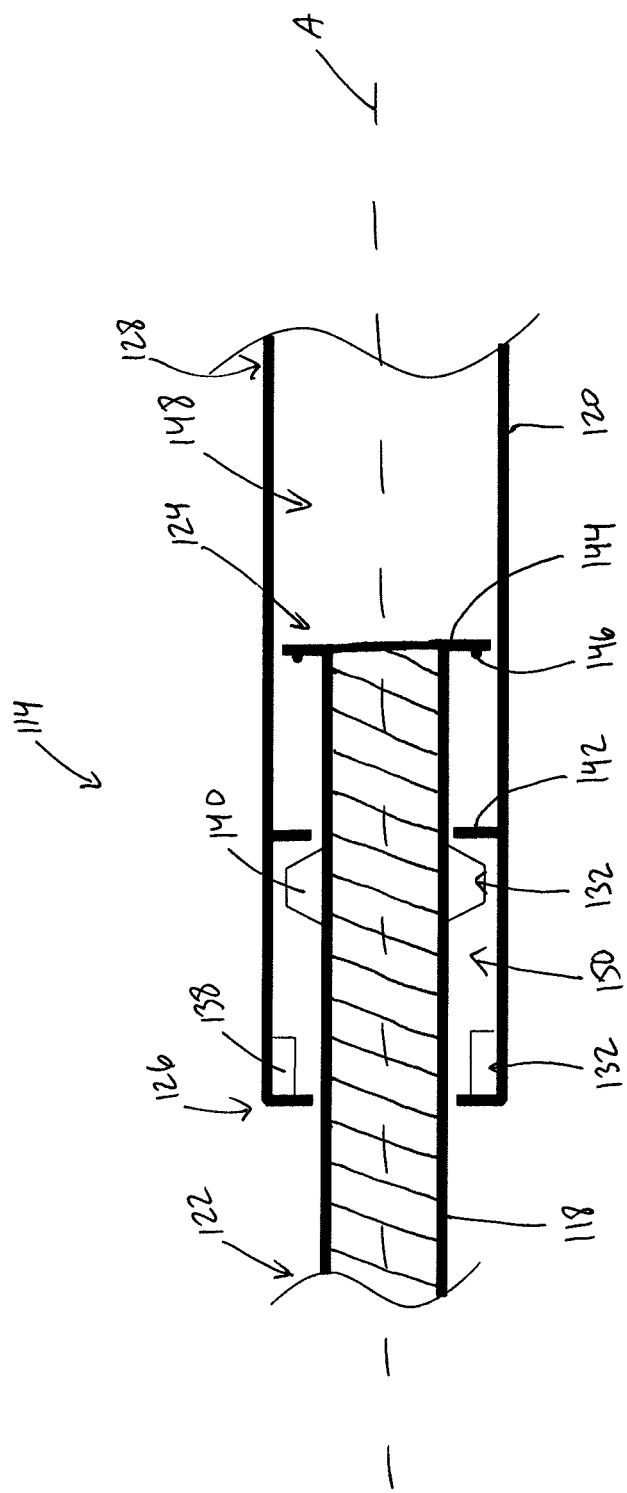
FIG. 4 shows a detailed side, cross-sectional view of an exemplary collapsible drill in a collapsed and disengaged position after complete penetration of a drilled material.

Turning now to FIGS. 3 and 4, side, partial and detailed cross-sectional views of an exemplary drill 100 are provided. In particular, the drill 100 is schematically illustrated in a collapsed and disengaged position after complete penetration of the drilled material 102, e.g., a wall, bone, cartilage, and the like. As can be seen from FIGS. 3 and 4, the tip 164 of the drill bit 112 has fully passed through the drilled material 102, including the inner surface 106 of the drilled material 102.

During drilling, when the drill bit 112 penetrates the hard substance of the drilled material 102, a sudden change in force or pressure occurs as imparted against the drill bit 112. The change in force can be detected by the sensor 152 positioned between the piston 114 and the motor section 116. Upon detection of the change in force imparted on the drill bit 112, a solenoid valve (not shown) located in the compressor 156 can open to vent the compressed air in the first chamber 148 to atmosphere through the outlet 160. The compressed air can thereby quickly exit from the piston 114.

The decrease in pressure within the first chamber 148 simultaneously decreases the force imparted on the radial protrusion 144 of the piston rod 118 against the ledge 142 of the cylinder 120, allowing translation of the piston rod 118 within the cylinder 120 along the central axis A. Thus, upon detection of the change in force imparted on the drill bit 112 and upon venting of the compressed air from the first chamber 148, the chuck 110, the drill bit 112 and the piston rod 118 can collapse or depress into the cylinder 120 of the piston 114 by translating along the central axis A until the teeth 140 of the piston rod 118 abut the ledge 142. In some embodiments, the distance the piston rod 118 can collapse or depress into the cylinder 120 can be variable based on, e.g., the area desired by the user, the force applied by the user, the potential "plunge" distance expected, and the like. In some embodiments, the distance the piston rod 118 can collapse or depress into the cylinder 120 can be adjusted by the user and/or the manufacturer to range from a distance in millimeters to a distance in centimeters.

Continued pressure or force imparted by a user against a handle (not shown) of the drill 100 can cause the drill 100 to move forward without a force being imparted by the drill bit 112. In particular, as the user continues to provide a force against the handle of the drill 100 to continue drilling, the chuck 110, the drill bit 112 and the piston rod 118 can be forced to collapse or translate into the cylinder 120 of the piston 114 due to the vented first chamber 148. Translation of the piston rod 118 along the central axis A in the direction of the ledge 142 due to the drop in pressure within the first chamber 148 forces the second pair of interlocking splines 132 between the piston rod 118 and the cylinder 120 to disengage. Disengagement of the second pair of interlocking splines 132 further releases the torque transfer from the cylinder 120 to the piston rod 118 and, in turn, the chuck 110 and the drill bit 112. Rotation of the drill bit 112 can therefore be prevented.

In some embodiments, stopping rotation of the drill bit 112 can also stop further advancement of the drill bit 112 into the inner cavity 108 of the drilled material 102 by preventing the drill bit 112 from cutting away at the structure within the inner cavity 108. In some embodiments, further advancement of the drill bit 112 into the inner cavity 108 of the drilled material 102 can be prevented by automatically and at least partially retracting the drill bit 112 out of the hole formed in the drilled material 102 when the piston rod 118 translates into the cylinder 120.

The user can release or reduce the force applied to the handle of the drill 100 before the piston 114 completely collapses or depresses, e.g., before the teeth 140 of the piston rod 118 abut the ledge 142, to prevent the stopped drill bit 112 from penetrating the soft matter, e.g., the nerves, blood vessels, and the like, within the inner cavity 108 beyond the hard substance of the drilled material 102 once the desired aperture has been formed. In terms of industrial uses, the user can release or reduce the force applied to the handle of the drill 100 before the piston 114 completely collapses to prevent the stopped drill bit 112 from penetrating the structures, e.g., the electrical wires, and the like, within the inner cavity 108 beyond the hard substance of the drilled material 102 once the desired aperture has been formed.

In some embodiments, the solenoid valve of the motor section 116 can open to a negative pressure reservoir (not shown). In some embodiments, the negative pressure reservoir can be generated electromechanically. Thus, when a drop in pressure is detected by the sensor 152, the compressed air within the first chamber 148 can be actively decompressed, the first chamber 148 can be actively collapsed, and the piston rod 118 can be sucked into the cylinder 120 of the piston 114 until the teeth 140 of the piston rod 118 abut the ledge 142. The chuck 110 and the drill bit 112 can thereby also be sucked in the direction of the cylinder 120 along the central axis A. Translation of the piston rod 118, the chuck 110 and the drill bit 112 can prevent further advancement of the drill bit 112 into the inner cavity 108 of the drilled material 102. In some embodiments, translation of the piston rod 118, the chuck 110 and the drill bit 112 can actively and/or automatically retract the drill bit 112 away from the drilled material 102 and/or any structures within the inner cavity 108. The force applied to the handle of the drill 100 can thereby be uncoupled from the force applied to the drill bit 112 to prevent damage to structures within the inner cavity 108 of the drilled material 112.

If a user wishes to drill further through the same or another drilled material 102, the first chamber 148 of the piston 114 can be refilled with compressed air through, e.g., actuation of a reset button, sensor detection, and the like. Although discussed herein as utilizing compressed air to fill the first chamber 148, those of ordinary skill in the art should understand that any similar mechanism using a piston-like design with, e.g., one or more fluids, one or more springs, and the like, can be utilized for extending and/or collapsing the drill 100.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A collapsible drill, comprising:
a chuck configured and dimensioned to receive a drill bit,
a piston including a pair of interlocking splines, and
a motor section,
wherein the motor section drives rotation of the piston and the chuck, and
wherein depression of the piston stops rotation of the chuck relative to the piston.

2. The collapsible drill according to claim 1, wherein the piston comprises a piston rod linearly translatable within a cylinder.

3. The collapsible drill according to claim 2, wherein the pair of interlocking splines comprises a plurality of grooves on the cylinder configured to interlock with a plurality of complementary teeth on the piston rod.

4. The collapsible drill according to claim 3, wherein the piston rod comprises a radial protrusion extending therefrom.

5. The collapsible drill according to claim 4, wherein the cylinder comprises an inner ledge configured and dimensioned to mate with the radial protrusion of the piston rod.

6. The collapsible drill according to claim 5, comprising an O-ring positioned between the radial protrusion and the inner ledge to form a sealed chamber within the cylinder.

7. The collapsible drill according to claim 6, wherein the motor section comprises a mechanism for filling the sealed chamber within the cylinder with compressed air and for venting the compressed air from the sealed chamber to atmosphere.

8. The collapsible drill according to claim 7, wherein venting the compressed air from the sealed chamber to atmosphere depresses the piston rod into the cylinder.

9. The collapsible drill according to claim 8, wherein depressing the piston rod into the cylinder disengages the plurality of grooves and the plurality of complementary teeth of the pair of interlocking splines.

10. The collapsible drill according to claim 9, wherein disengaging the plurality of grooves and the plurality of complementary teeth of the pair of interlocking splines stops rotation of the chuck relative to the piston.

11. The collapsible drill according to claim 8, wherein depressing the piston rod into the cylinder retracts the drill bit from a material.

12. The collapsible drill according to claim 2, comprising a second pair of interlocking splines positioned between the cylinder and the motor section.

13. A method of drilling into a material, comprising:
providing a collapsible drill, the collapsible drill including (i) a chuck configured and dimensioned to receive a drill bit, (ii) a piston including a pair of interlocking splines, and (iii) a motor section,
driving rotation of the piston and the chuck with the motor section, and
depressing the piston to stop rotation of the chuck relative to the piston.

14. The method according to claim 13, comprising filling a sealed chamber within a cylinder of the piston with compressed air to position a radial protrusion extending from a piston rod against an inner ledge of the cylinder.

15. The method according to claim 14, comprising maintaining a pressure within the sealed chamber to maintain the drill bit in an extended position.

16. The method according to claim 14, comprising interlocking a plurality of grooves on a cylinder of the piston with a plurality of complementary teeth on a piston rod of the piston of the pair of interlocking splines to drive rotation of the chuck relative to the piston.

17. The method according to claim 14, comprising venting the sealed chamber to depress the piston rod into the cylinder.

18. The method according to claim 17, wherein depressing the piston rod into the cylinder comprises disengaging a plurality of grooves on the cylinder with a plurality of complementary teeth on the piston rod of the pair of interlocking splines.

19. The method according to claim 18, wherein disengaging the plurality of grooves on the cylinder with the plurality of complementary teeth on the piston rod of the pair of interlocking splines comprises stopping rotation of the chuck relative to the piston.

20. The method according to claim 17, wherein depressing the piston rod into the cylinder comprises retracting the drill bit from the material.

\* \* \* \* \*